US00PP17550P2

(12) United States Plant Patent

Parthasarathy et al.

(10) Patent No.: US PP17,550 P2

(45) Date of Patent: Apr. 3, 2007

(54) *AGLAONEMA* PLANT NAMED 'KEY LARGO'

(50) Latin Name: *Aglaonema hybrida*
Varietal Denomination: Key Largo

(76) Inventors: Gopalaswamy Parthasarathy, "Srinivas", 237/46, Fifth Main Road, Chamrajpet, Bangalore 560018 (IN); Parthasarathy Mukundan, "Srinivas", 237/46, Fifth Main Road, Chamrajpet, Bangalore 560018 (IN)

( * ) Notice: Subject to any disclaimer, the term of this patent is extended or adjusted under 35 U.S.C. 154(b) by 27 days.

(21) Appl. No.: 11/174,969

(22) Filed: Jul. 5, 2005

(51) Int. Cl.
*A01H 5/00* (2006.01)

(52) U.S. Cl. ..... Plt./376

(58) Field of Classification Search ..... Plt./376
See application file for complete search history.

(56) References Cited

U.S. PATENT DOCUMENTS

PP8,975 P * 11/1994 Brown ..... Plt./376
PP10,280 P * 3/1998 Brown ..... Plt./376

OTHER PUBLICATIONS http://www.aroid.org/gallery/mukundan/.*

* cited by examiner

*Primary Examiner*—Wendy Haas
(74) *Attorney, Agent, or Firm*—C. A. Whealy

(57) ABSTRACT

A new and distinct cultivar of *Aglaonema* plant named 'Key Largo', characterized by its compact, upright and outwardly arching plant form; vigorous growth habit; relatively short internodes; full, dense and bushy appearance; oblong leaves with cuspidate apices; upper leaf surfaces dark green in color with distinct and contrasting silvery gray centers and random silver-colored flecks and spots; short green-colored leaf petiodes; and tolerance to low temperatures.

1 Drawing Sheet

Botanical designation: *Aglaonema hybrida.*
Cultivar denomination: 'Key Largo'.

BACKGROUND OF THE INVENTION

The present Invention relates to a new and distinct cultivar of *Aglaonema* plant, botanically known as *Aglaonema hybrida* and hereinafter referred to by the name 'Key Largo'.

The new *Aglaonema* is the result of a planned breeding program conducted by the Inventors in Chamrajpet, Bangalore, India. The objective of the breeding program is to create near vigorous *Aglaonema* cultivars with compact and dense plant habit, unique leaf coloration, interesting leaf shapes, resistance to pathogens and pests common to *Algaonemas* and tolerance to low temperatures.

The new *Aglaonema* originated from a cross-pollination made by the Inventors on Jun. 12, 1985 of the *Aglaonema nitidum* (Jack) Kunth. *f. cinereum* Jervis cultivar Ernesto's Favorite, not patented, as the female, or seed, parent with the *Aglaonema commutatum* var. *maculatum* cultivar Malay Lady, not patented, as the male, or pollen, parent. The new *Aglaonema* was discovered and selected by the Inventors in 1986 as a single plant within the progeny of the stated cross-pollination in a controlled environment in Chamrajpet, Bangalore, India. The new *Aglaonema* was selected on the basis of its plant habit, leaf shape and uniquely colored foliage.

Asexual propagation of the new cultivar by divisions and cuttings since January, 1989 in a controlled environment in Chamrajpet, Bangalore, India, has shown that the unique features of this new *Aglaonema* are stable and reproduced true to type in successive generations.

SUMMARY OF THE INVENTION

The following traits have been repeatedly observed and are determined to be the unique characteristics of 'Key Largo'. These characteristics in combination distinguish 'Key Largo' as a new and distinct cultivar of *Aglaonema:*

1. Compact, upright and outwardly arching plant form.
2. Vigorous growth habit.
3. Relatively short internodes; full, dense and bushy appearance.
4. Oblong leaves with cuspidate apices.
5. Unique leaf coloration; upper leaf surfaces dark green in color with distinct and contrasting silvery gray centers and random silver-colored flecks and spots.
6. Short green-colored leaf petioles.
7. Tolerant to low temperatures.

In side-by-side comparisons conducted by the Inventors in Chamrajpet, Bangalore, India, plants of the new *Aglaonema* differed from plants of the female parent, the cultivar Ernesto's Favorite, in the following characteristics:

1. Plants of the new *Aglaonema* were more compact than plants of the cultivar Ernesto's Favorite.
2. Plants of the new *Aglaonema* were denser than plants of the cultivar Ernesto's Favorite.
3. Leaves of plants of the new *Aglaonema* were broader than leaves of plants of the cultivar Ernesto's Favorite.
4. Plants of the new *Aglaonema* and the cultivar Ernesto's Favorite differed in leaf and leaf petiole coloration.
5. Plants of the new *Aglaonema* were more tolerant to low temperatures than plants of the cultivar Ernesto's Favorite.

In side-by-side comparisons conducted by the Inventors in Chamrajpet, Bangalore, India, plants of the new *Aglaonema* differed from plants of the male parent, the cultivar Malay Lady, in the following characteristics:

1. Plants of the new *Aglaonema* were more vigorous than plants of the cultivar Malay Lady.
2. Plants of the new *Aglaonema* were denser than plants of the cultivar Malay Lady.
3. Leaves of plants of the new *Aglaonema* were broader than leaves of plants of the cultivar Malay Lady.
4. Plants of the new *Aglaonema* and the cultivar Malay Lady differed in leaf and leaf petiole coloration.
5. Plants of the new *Aglaonema* were more tolerant to low temperatures than plants of the cultivar Malay Lady.

Plants of the new *Aglaonema* can be compared to plants of the cultivar Rhapsody in Green, disclosed in U.S. Plant Pat. No. 8,975. In side-by-side comparisons conducted in Chamrajpet, Bangalore, India, plants of the new *Aglaonema* differed from plants of the *Agalonema* cultivar Rhapsody in Green in the following characteristics:

1. Leaves of plants of the new *Aglaonema* were held mostly horizontally whereas leaves of plants of the cultivar Rhapsody in Green were held mostly erect.
2. Leaves of plants of the new *Aglaonema* were broader and had shorter petioles than leaves of plants of the cultivar Rhapsody in Green.
3. Plants of the new *Aglaonema* and the cultivar Rhapsody in Green differed in leaf and leaf petiole coloration.

Plants of the new *Aglaonema* can also be compared to plants of the cultivar Black Lance, disclosed in U.S. Plant Pat. No. 10,280. In side-by-side comparisons conducted in Chamrajpet, Bangalore, India, plants of the new *Aglaonema* differed from plants of the *Aglaonema* cultivar Black Lance in the following characteristics:

1. Leaves of plants of the new *Aglaonema* were broader and had shorter petioles than leaves of plants of the cultivar Black Lance.
2. Plants of the new *Aglaonema* and the cultivar Black Lance differed in leaf and leaf petiole coloration.

BRIEF DESCRIPTION OF THE PHOTOGRAPH

The accompanying colored photograph illustrates the overall appearance of the new *Aglaonema,* showing the colors as true as it is reasonably possible to obtain in colored reproductions of this type. Colors in the photograph may differ slightly from the color values cited in the detailed botanical description which accurately describe the colors of the new *Aglaonema.* The photograph comprises a side perspective view of a typical plant of 'Key Largo'.

DETAILED BOTANICAL DESCRIPTION

The cultivar Key Largo has not been observed under all possible environmental conditions. The phenotype may vary somewhat with variations in environment such as temperature and light intensity without, however, any variance in genotype.

The following observations and measurements describe plants of the new *Aglaonema* that were grown in 25-cm containers, in Homestead, Fla., in a polypropylene-covered shadehouse with light levels about 2,500 foot-candles. During the production of the plants, temperatures ranged from 2° C. to 43° C. Plants used for the photograph and description were about 14 months from planting. Color references are made to The Royal Horticultural Society Colour Chart, 1995 Edition, except where general terms of ordinary dictionary significance are used.

Botanical classification: *Aglaonema hybrida* cultivar Key Largo.

Parentage:

*Female, or seed, parent.*—*Aglaonema nitidum* (Jack) Kunth *f. cinereum* Jervis cultivar Ernesto's Favorite, not patented.

*Male, or pollen, parent.*—*Aglaonema commutatum* var. *maculatum* cultivar Malay Lady, not patented.

Propagation:

*Type.*—by divisions.

*Time to initiate roots.*—Summer: About 18 to 20 days at 25° C. to 36° C. Winter: About 30 to 35 days at 15° to 28° C.

*Time to produce a rooted plant.*—Summer: About 30 to 35 days at 25° C. to 36° C. Winter: About 40 to 45 days at 15° C. to 28° C.

*Root description.*—Thick, fibrous, fleshy; off-white in color.

*Rooting habit.*—Freely-branching; dense.

Plant description:

*Plant form.*—Erect when young, becoming outwardly arching as leaves develop; inverted triangle, symmetrical and uniform.

*Vigor/growth rate.*—Vigorous; relatively rapid growth rate. Plant size appropriate for 25-cm containers.

*Growth habit.*—Plants typically produce about two to three offshoots per plant; full, dense and bushy appearance.

*Plant height.*—About 43 cm.

*Plant width (spread).*—About 57 cm.

*Stem description.*—Length: About 18 cm. Diameter: About 2.25 cm. Internode length: About 1.75 cm. Aspect: Upright. Strength: Good. Color: 147A.

*Foliage description.*—Appearance: Single; clasping. Length: About 22.5 cm. Width: About 9.2 cm. Shape: Oblong. Apex: Cuspidate. Base: Obtuse. Margin: Entire; undulating. Orientation: Initially upright to roughly horizontal. Texture: Smooth, glabrous; thick and leathery. Veins: Prominent on lower surface. Venation pattern: Pinnate. Color: Developing and fully expanded leaves, upper surface: Ground color, darker than 147A; central area and random spots, close to 191A. Developing and fully expanded leaves, lower surface: Lighter green than 147A. Venation, upper surface: Same as lamina. Venation, lower surface: Close to 146B to 146C. Petiole: Aspect: Erect to outwardly bent. Length: About 11.5 cm. Diameter, distal: About 5 mm. Diameter, proximal: About 1.75 mm. Wing length: About 9.4 cm. Wing diameter: About 7 mm. Color, developing and fully expanded leaves, petiole and wing: Close to 146B.

Inflorescence description: Inflorescence development has not been observed on plants of the new *Aglaonema* grown under shadehouse production conditions.

Disease/pest resistance: Plants of the new *Aglaonema* have been observed to be resistant to pathogens common to *Aglaonema* such as *Xanthomonas* and *Phytophthora.* Plants of the new *Aglaonema* have not been observed to be resistant to pests and other pathogens common to *Aglaonema.*

Weather tolerance: Plants of the new *Aglaonema* have been observed to be tolerant to wind, rain and temperatures ranging from 2° C. to 43° C.

It is claimed:

1. A new and distinct cultivar of *Aglaonema* plant named 'Key Largo', as illustrated and described.

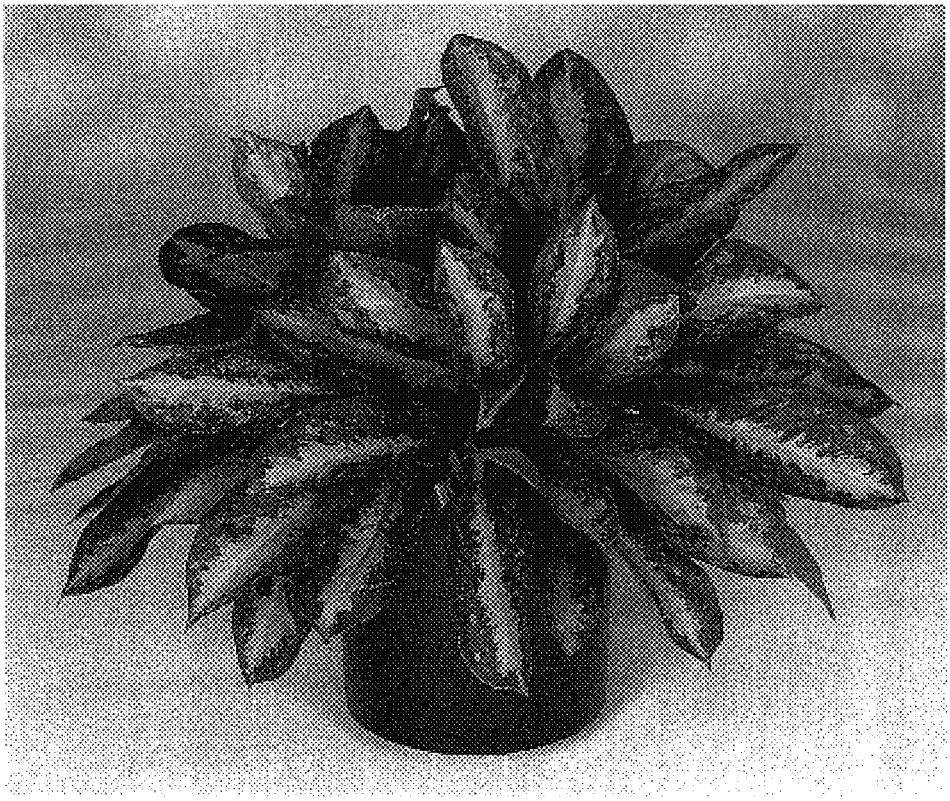

* * * * *